United States Patent
Dias

(10) Patent No.: US 9,528,097 B2
(45) Date of Patent: Dec. 27, 2016

(54) METHOD OF EXTRACTION OF AN ENZYME FROM PLANT OR ANIMAL TISSUE

(71) Applicant: Syngenta Participations AG, Basel (CH)

(72) Inventor: Mahathelge Dilip Dias, Durham, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 13/768,164

(22) Filed: Feb. 15, 2013

(65) Prior Publication Data

US 2014/0234871 A1 Aug. 21, 2014

(51) Int. Cl.
*C12N 9/32* (2006.01)

(52) U.S. Cl.
CPC ..... *C12N 9/2422* (2013.01); *C12Y 302/01001* (2013.01)

(58) Field of Classification Search
None
See application file for complete search history.

(56) References Cited

U.S. PATENT DOCUMENTS

| | | |
|---|---|---|
| 7,102,057 B2 | 9/2006 | Lanahan et al. |
| 7,635,799 B2 | 12/2009 | Johnson et al. |
| 7,914,993 B2 | 3/2011 | Batie et al. |

OTHER PUBLICATIONS

Smilowitz et al., Association of newly synthesized major fl coat protein with infected host cell inner membrane., Journal of Supramolecular Structure (1972), vol. 1, Issue 1, pp. 8-18.*
Van den Bulcke et al., Detection of genetically modified plant products by protein strip testing: an evaluation of real-life samples, Eur Food Res Technol (2007), vol. 225, pp. 49-57.*
Hu et al., Short communication: In vitro ruminal fermentability of a modified corn cultivar expressing a thermotolerant α-amylase., Journal of Dairy Science (2010), vol. 93, pp. 4846-4849.*
Megazyme Total Starch Assay Procedure (2011).*
Holck, A. L. Genetically Modified Organisms Detection by Analytical and Spectroscopical Methods. Encyclopedia of Analytical Chemistry (Epub: Jun. 15, 2012), pp. 1-35.*

* cited by examiner

*Primary Examiner* — Alexander Kim
(74) *Attorney, Agent, or Firm* — Yoshimi D. Barron

(57) ABSTRACT

This invention provides a method for the extraction and detection of a peptide from transgenic plant tissues wherein a non-immunogenic solubility-promoting compound is used to release the enzyme into the solution fraction during the purification process. In some embodiments, this invention provides a method for the extraction and detection of the enzyme Amy797E, which is a heterologous thermo-tolerant α-amylase, from the tissues of corn event 3272 using a non-immunogenic amylase during the purification process. This invention allows for a limit of detection of 1:1000 of Amy797E in an enzyme-linked immunosorbent assay (ELISA).

1 Claim, No Drawings

METHOD OF EXTRACTION OF AN ENZYME FROM PLANT OR ANIMAL TISSUE

FIELD OF THE INVENTION

The present invention relates to techniques for extraction, purification, and detection of enzymes from living tissue, and is further related to extraction, purification, and detection of heterologous enzymes from transgenic plant tissue.

BACKGROUND

Enzymes are used to process a variety of agricultural products such as wood, fruits and vegetables, starches, juices, and the like. Typically, processing enzymes are produced and recovered on an industrial scale from various sources, such as microbial fermentation (*Bacillus* α-amylase), or isolation from plants (coffee β-galactosidase or papain from plant parts). Enzyme preparations are used in different processing applications by mixing the enzyme and the substrate under the appropriate conditions of moisture, temperature, time, and mechanical mixing such that the enzymatic reaction is achieved in a commercially viable manner. One area where enzymes play an important role is in the area of corn milling.
Today corn is milled to obtain cornstarch and other corn-milling co-products such as corn gluten feed, corn gluten meal, and corn oil. The starch obtained from the process is often further processed into other products such as derivatized starches and sugars, or fermented to make a variety of products including alcohols or lactic acid.

The process of starch recovery from corn grain is well known and involves a wet-milling process. Corn wet-milling involves many time consuming and costly steps, which include steeping the corn kernel, grinding the corn kernel, and separating the components of the kernel. Dry-mill processes that make fermentable sugars (and then ethanol, for example) from cornstarch facilitate efficient contacting of exogenous enzymes with starch. These processes are less capital intensive than wet-milling but significant cost advantages are still desirable, as often the co-products derived from these processes are not as valuable as those derived from wet-milling.

Thus, for dry milling, there is a need for a method that improves the efficiency of the process and/or increases the value of the co-products. For wet milling, there is a need for a method of processing starch that does not require the equipment necessary for prolonged steeping, grinding, milling, and/or separating the components of the kernel. For example, there is a need to modify or eliminate the steeping step in wet milling as this would reduce the amount of waste water requiring disposal, thereby saving energy and time, and increasing mill capacity (kernels would spend less time in steep tanks). There is also a need to eliminate or improve the process of separating the starch-containing endosperm from the embryo.

The present invention relates to a transgenic corn (*Zea mays*) plant, event 3272 (Johnson et al, U.S. Pat. No. 7,635,799; incorporated by reference), that has incorporated into its genome a synthetic α-amylase gene (amy797E), encoding a thermostable Amy797E α-amylase capable of processing starch in plants. α-amylase enzymes act on starch and related polysaccharides and oligosaccharides in a random manner, performing endohydrolysis of $(1{\rightarrow}4)$-α-D-glucosidic linkages in polysaccharides containing three or more $(1{\rightarrow}4)$-α-linked D-glucose units, such as those found in starch. Upon expression and activation of the Amy797E α-amylase, the enzyme processes the starch substrate found within the plant or plant tissue. This processing results in an altered composition which facilitates plant and grain processing for milling, thereby making a significant improvement in processing corn plants or plant parts for fermentation compared to corn plants which do not express amy797E (see, for example, Lanahan et al., U.S. Pat. No. 7,102,057 and Batie et al., U.S. Pat. No. 7,914,993, which are incorporated by reference).

A highly sensitive method for detecting the Amy797E α-amylase from transgenic events is necessary for use in environmental monitoring, monitoring traits in crops in the field, or monitoring products derived from a crop harvest, as well as for use in ensuring compliance of parties subject to contractual terms. It is ideal to have a limit of detection of Amy797E protein of less than 0.1%. In other words, a method of detection is needed to detect less than one kernel of corn event 3272 per 1000 kernels.

Additionally, certain applications of milling of event 3272 require mixing event 3272 corn or corn seed with corn or corn seed that is not event 3272 (see, for example, U.S. Pat. No. 7,914,993). This mixing is required so that an optimal amount of Amy797E α-amylase per unit of corn or corn seed is achieved. A highly sensitive method of Amy979E detection would also benefit users who need to measure the amount of Amy797E present in a given amount of event 3272 corn or corn seed.

It is standard in the art to detect the presence of a specific polypeptide of interest using an antibody specific to the polypeptide of interest in an ELISA (enzyme-linked immunosorbent assay). An ELISA is a method for detecting a polypeptide of interest in a biological sample, the method typically comprising: (a) extracting protein from a biological sample; (b) assaying the extracted protein using an immunological method comprising an antibody specific for the polypeptide of interest; and (c) detecting the binding of said antibody to the polypeptide of interest. Detection is typically measured via an enzyme which is linked to a secondary antibody. The enzyme can metabolize a colorless substrate into a colored product. The optical density is measured, and this is proportional to the amount of colored product and to the amount of the polypeptide of interest present in the sample.

The ELISA method described above is known to one skilled in the art for the detection of transgenic polypeptides in plants. However, the polypeptide of interest here, Amy797E, presents an unusual challenge because its native substrate, starch, is found within the plant cell, and Amy797E tends to be pre-bound to its substrate in an inactive form. Starch is typically insoluble and comes out in the insoluble fraction during standard purification. Using the insoluble fraction for ELISA is undesirable, because the insoluble fraction significantly reduces the availability of the polypeptides, enzymes or other substrates bound or otherwise associated thereto for ELISA. Although not all of Amy797E in the plant cell is pre-bound to insoluble starch, it is preferred to release this pre-bound Amy797E to increase the limit of quantification and the limit of detection in a standard ELISA. The present invention solves this problem.

SUMMARY OF THE INVENTION

The present invention is drawn to a novel method of extracting a polypeptide of interest from a biological sample. The present invention includes a method for extraction of a polypeptide of interest which binds to an insoluble substrate in the context of a cell. This method of extraction from the biological sample a polypeptide bound to an insoluble substrate comprises initially homogenizing the biological sample in the presence of extraction buffer and a solubility-promoting compound. It is preferred that the solubility-promoting compound be non-immunoreactive. The sample is incubated to allow for solubilization of the polypeptide of interest. Finally, the sample is centrifuged to separate the soluble and insoluble fractions; the polypeptide of interest separates into the soluble fraction. Detection of the polypeptide in the soluble fraction is by any means known in the art, including by immunoassay such as ELISA, sandwich ELISA, ELISA dipstick, Lateral Flow Immunochromatographic Assay, magnetic immunoassay, radioimmunoassay, or fluorescent immunoassay.

The present invention is drawn to a novel method of extracting a polypeptide of interest from plant tissue. The present invention is a novel approach for extraction of a polypeptide of interest which binds to an insoluble substrate in the context of a plant cell. This method of extracting from plant tissue a polypeptide bound to an insoluble substrate comprises initially homogenizing the tissue sample in the presence of extraction buffer and a solubility-promoting compound. It is preferred that the solubility-promoting compound be non-immunoreactive. The sample is incubated to allow for solubilization of the polypeptide. Finally, the sample is centrifuged to separate the soluble and insoluble fractions; the polypeptide of interest separates into the soluble fraction. From here, the soluble polypeptide of interest is available for detection. Detection of the polypeptide in the soluble fraction is by any means known in the art, including by immunoassay such as ELISA, sandwich ELISA, ELISA dipstick, Lateral Flow Immunochromatographic Assay, magnetic immunoassay, radioimmunoas say, or fluorescent immunoassay.

One aspect of the invention is directed to extracting a polypeptide which interacts with an insoluble macromolecule within a living cell using a non-immunoreactive solubility-promoting compound.

One aspect of the invention is directed to extracting a heterologous enzyme which interacts with an insoluble macromolecule within a living cell using a non-immunoreactive solubility-promoting compound.

One aspect of the invention is directed to extracting a heterologous enzyme bound to an insoluble substrate within a living cell using a non-immunoreactive solubility-promoting compound.

One aspect of the invention is directed to extracting a heterologous enzyme which binds to an insoluble substrate within a living cell using a non-immunoreactive solubility-promoting compound which is a macromolecule-degrading enzyme.

One aspect of the invention is directed to extracting a heterologous enzyme which binds to an insoluble substrate within a living cell using a non-immunoreactive solubility-promoting compound which is a substrate-degrading enzyme.

One aspect of the invention is directed to extracting a heterologous amylase using a non-immunoreactive substrate-degrading enzyme.

One aspect of the invention is directed to plant tissue from the transgenic corn event 3272, which heterologously expresses the α-amylase Amy797E, using a non-immunoreactive substrate-degrading enzyme.

One aspect of the invention is directed to plant tissue from the transgenic corn event 3272, which heterologously expresses the α-amylase Amy797E, using a non-immunoreactive amylase.

One aspect of the invention is directed to plant tissue from the transgenic corn event 3272, and homogenizing the plant tissue sample in the presence of extraction buffer and a non-immunoreactive amylase. The sample is incubated to allow the non-immunoreactive amylase to degrade the starch substrate, thereby releasing Amy797E from its insoluble substrate. Finally, the sample is centrifuged to separate the soluble and insoluble fractions; Amy797E fractionates into the soluble fraction. From here, Amy797E is available for detection by immunoassay such as ELISA, sandwich ELISA, ELISA dipstick, Lateral Flow Immunochromatographic Assay, magnetic immunoassay, radioimmunoassay, or fluorescent immunoassay.

One aspect of the invention is directed to plant tissue from the transgenic corn event 3272, and homogenizing the plant tissue sample in the presence of extraction buffer and a non-immunoreactive amylase. The sample is then incubated at 89-95° C. for 15 minutes to allow the non-immunoreactive amylase to degrade the starch substrate. Finally, the sample is centrifuged to separate the soluble and insoluble fractions; Amy797E fractionates into the soluble fraction. From here, Amy797E is available for detection by immunoassay such as ELISA, sandwich ELISA, ELISA dipstick, Lateral Flow Immunochromatographic Assay, magnetic immunoassay, radioimmunoassay, or fluorescent immunoassay.

DEFINITIONS

The following definitions and methods are provided to better define the present invention and to guide those of ordinary skill in the art in the practice of the present invention. Unless otherwise defined, all technical and scientific terms used herein have the same meaning as commonly understood by one of ordinary skill in the relevant art. The terminology used in the description of the invention herein is for the purpose of describing particular embodiments only and is not intended to be limiting of the invention.

All publications, patent applications, patents, and other references mentioned herein are incorporated by reference in their entirety.

The term "transgene" as used herein, refers to any nucleic acid sequence used in the transformation of a plant, animal, or other organism. Thus, a transgene can be a coding sequence, a non-coding sequence, a cDNA, a gene or fragment or portion thereof, a genomic sequence, a regulatory element and the like. A "transgenic" organism, such as a transgenic plant, transgenic microorganism, or transgenic animal, is an organism into which a transgene has been delivered or introduced and the transgene can be expressed in the transgenic organism to produce a product, the presence of which can impart an effect and/or a phenotype in the organism.

A transgenic "event" refers to a transgenic plant produced by transformation and regeneration of a single plant cell with heterologous DNA, such as an expression cassette that includes a gene of interest. The term "event" also refers to progeny produced by the event.

The terms "polypeptide," "protein," and "peptide" refer to a chain of covalently linked amino acids. In general, the term "peptide" can refer to shorter chains of amino acids (e.g., 2-50 amino acids); however, all three terms overlap with respect to the length of the amino acid chain. As used herein, the terms "protein" and "polypeptide" are used interchangeably and encompass peptides, unless indicated otherwise. Polypeptides, proteins, and peptides may comprise naturally occurring amino acids, non-naturally occurring amino acids, or a combination of both. Non-naturally occurring polypeptides, proteins, peptides, amino acids may comprise heterologous nucleic acids. The polypeptides, proteins, and peptides may be isolated from sources (e.g., cells or tissues) in which they naturally occur, produced recombinantly in cells in vivo or in vitro or in a test tube in vitro, or synthesized chemically. Such techniques are known to those skilled in the art. See, e.g., Sambrook et al., Molecular Cloning: A Laboratory Manual 2nd Ed. (Cold Spring Harbor, N.Y., 1989); Ausubel et al. Current Protocols in Molecular Biology (Green Publishing Associates, Inc. and John Wiley & Sons, Inc., New York). A "polypeptide," "protein," or "peptide" may comprise an enzyme.

A "heterologous" nucleic acid sequence is a sequence that is not naturally associated with the host cell into which it is introduced, including non-naturally occurring multiple copies of a naturally occurring sequence. A "heterologous" or "heterologously expressed" polypeptide or enzyme is that which is encoded by the heterologous nucleic acid sequence and expressed by that host cell.

"Amy797E" refers to the thermostable 797GL3 α-amylase encoded by the amy797E gene (Lanahan et al., U.S. Pat. No. 7,102,057) and expressed in corn event 3272 (Johnson et al., U.S. Pat. No. 7,635,799).

"Corn event 3272," "maize event 3272," or "event 3272" refer to the transgenic maize event described in Johnson et al., U.S. Pat. No. 7,635,799.

A "macromolecule" is a very large molecule, such as a polymer or protein, consisting of many smaller structural units linked together. A "macromolecule" can refer to biopolymers such as polynucleotides, polypeptides, and polysaccharides. A "macromolecule" can also refer to synthetic polymers, such as plastics, synthetic fibers, or carbon nanotubes. A macromolecule can include within its meaning a "substrate" molecule. A macromolecule can include molecules such as deoxyribonucleic acids (DNA), ribonucleic acids (RNA), polypeptides, cellulose, xylan, arabinoxylan, arabinogalactan, pectin, hemicellulose, cutin, and lignin.

A "substrate" is a molecule upon which an enzyme acts to produce a product. Enzymes catalyze chemical reactions involving substrates. A substrate can include molecules such as deoxyribonucleic acids (DNA), ribonucleic acids (RNA), polypeptides, cellulose, xylan, arabinoxylan, arabinogalactan, pectin, hemicellulose, cutin, and lignin.

A "non-immunoreactive" or "non-immunogenic" compound or polypeptide refers to a compound or polypeptide which is not recognized by the antibody raised against a polypeptide of interest.

For example, a non-immunogenic compound is not recognized by the antibody used in the ELISA to detect a polypeptide of interest.

An "immunoassay" refers to a biochemical test that measures the presence or concentration of a macromolecule in solution through the use of an antibody or immunoglobulin.

DETAILED DESCRIPTION OF THE INVENTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

The present invention includes a novel method of extracting a polypeptide of interest from a biological sample. The present invention includes a method for extraction of a polypeptide of interest bound to an insoluble substrate in the context of a cell. This method of extracting from the biological sample a polypeptide bound to an insoluble substrate comprises initially homogenizing the biological sample in the presence of extraction buffer and a solubility-promoting compound. It is preferred that the solubility-promoting compound be non-immunoreactive. The sample is incubated to allow for solubilization of the polypeptide of interest. Finally, the sample is centrifuged to separate the soluble and insoluble fractions; the polypeptide of interest separates into the soluble fraction. Detection of the polypeptide in the soluble fraction is by any means known in the art, including by immunoassay such as ELISA, sandwich ELISA, ELISA dipstick, Lateral Flow Immunochromatographic Assay, magnetic immunoassay, radioimmunoassay, or fluorescent immunoassay.

The present invention is a method for extraction and detection of a polypeptide expressed in plant tissue. In particular, this method is directed toward polypeptides which may be interacting with an insoluble macromolecule found within the host cell, including but not limited to polysaccharides such as starch or plant cell wall components such as cellulose, xylan, arabinoxylan, arabinogalactan, pectin, hemicellulose, and lignin. Examples of such polypeptides include but are not limited to amylolytic enzymes such as α-amylases and β-amylases, or cell wall degrading enzymes such as cellulases, xylanases, pectinases, pectin methylesterases, polygalacturonases, xylosidases, hemicellulases, glucanases, galactanases, or arabinosidases, or proteases, cutinases, or lignases.

The present invention further includes a method for extraction and detection of a heterologously expressed enzyme from transgenic plant tissue. The present invention includes a method directed toward heterologously expressed enzymes which may be pre-bound to an insoluble substrate found within the host cell, including but not limited to starch or plant cell wall components such as cellulose, xylan, arabinoxylan, arabinogalactan, pectin, hemicellulose, and lignin. Examples of potentially such enzymes include but are not limited to amylolytic enzymes such as α-amylases and β-amylases, or cell wall degrading enzymes such as cellulases, xylanases, pectinases, pectin methylesterases, polygalacturonases, xylosidases, hemicellulases, glucanases, or arabinosidases, or proteases, cutinases, or lignases.

The present invention uses a solubility-promoting compound in the extraction buffer to increase the amount of heterologously expressed enzyme found in the soluble fraction following purification. It is preferred that this compound be non-immunogenic so that it is not recognized by the antibodies used to detect the polypeptide of interest, for example in an ELISA. Usage of a non-immunogenic compound allows the method to not require a step for the removal of a possible immunogenic compound prior to analysis of the sample by ELISA.

Examples of non-immunogenic, solubility-promoting compounds include but are not limited to substrate-degrading compounds, such as an enzyme which can degrade insoluble macromolecules. Enzymes which can degrade insoluble macromolecules, including but not limited to polysaccharides, such as starch or plant cell wall components such as cellulose, xylan, arabinoxylan, arabinogalactan, pectin, hemicellulose, and lignin, include but are not limited to amylolytic enzymes such as amylases, or cell wall degrading enzymes such as cellulases, xylanases, pectinases, pectin methylesterases, polygalacturonases, xylosidases, hemicellulases, glucanases, or arabinosidases, or proteases, cutinases, or lignases.

Although the following examples use ground kernels, the tissue from any part of the maize plant, including but not limited to leaf, root, kernel, or pollen, may be used in this assay. Additionally, this assay may be used for animal diet samples, including but not limited to Starter, Grower, or Finisher Broiler diets, or Rat diet. Additionally, this assay may be used for other biological samples, including but not limiting to tissue samples from any part of any plant, insect, or animal, including blood, serum, or cell culture. Additionally, this assay may be used for microorganismal cultures, including but not limited to such microorganisms as fungi, yeast, bacteria, or algae.

Example 1

Addition of Amylase Results in Reduced Lower Limit of Quantification and Higher Sensitivity 30 mg of ground kernels from maize event 3272 were mixed with 3 ml of 1×PBS-T (phosphate buffered saline with Tween) solution. The "Control" sample did not have amylase added; the "+amylase" sample had 0.05% of a commercially available, non-immunoreactive amylase added to the 1×PBS-T solution. Four Control samples were prepared, and 9+ amylase samples were prepared. The samples were homogenized using the Omni-Prep Homogenizer at 30 K rpm for 30 seconds, twice. The samples were then heat treated for 15 minutes at 90° C. for 15 minutes. Next, the samples were centrifuged at 10,000×g for 15 minutes at room temperature. The soluble fraction, which is the supernatant, was taken, dilutions were made, and ELISA was performed using a commercially available kit from EnviroLogix containing an antibody specific to Amy797E. The following table displays the Lower Limit of Quantification (LLOQ) for the ELISA from each sample, expressed for each sample as the dilution factor and as µg Amy797E per g tissue. The LLOQ represents the limit at which the ELISA can accurately measure how much of the polypeptide of interest is present.

| Sample | Dilution factor | LLOQ (µg/g) |
|---|---|---|
| Control | >128 | not able to determine |
| +amylase | 1 | 0.125 |

The Control samples, which do not have an amylase added, had a high dilution factor of greater than 128. This means that the samples were diluted 128-fold in an effort to reduce interference from cellular carbohydrates. This relatively high interference is likely due to relatively low amounts of Amy797E in the soluble fraction available for ELISA. At a 128-fold dilution, a minimum dilution factor still could not be determined. Additionally, the dilution factor was so great than an accurate LLOQ could not be calculated. When amylase is added to the samples, a dilution factor of only 1 is required, likely due to the increase of Amy797E now available in the soluble fraction. The relatively low LLOQ is also indicative of the sensitivity of the method.

Example 2

Detection of One Maize Event 3272 Kernel in 1000 Non-Transgenic Kernels

In the following example, a positive sample was prepared by mixing one kernel of maize event 3272 with 1000 kernels of non-transgenic maize. The kernels were then ground into a powder. As a negative control, 1000 kernels of non-transgenic maize were also ground into a powder. 6 samples of positive and 6 samples of control ground kernels were prepared. Positive and control samples were randomized and a blind experiment was performed.

For each sample, 30 mg of ground kernels were mixed with 3 ml of 1×PBS-T (phosphate buffered saline with Tween) solution and 0.05% of a commercially available, non-immunoreactive amylase; As in Example 1, the samples were homogenized, heat treated, and centrifuged. For each sample, the undiluted supernatant, which is the soluble fraction, was then taken and ELISA was performed in duplicate using a commercially available kit from EnviroLogix containing an antibody specific to Amy797E. A reference known to contain 0.0313 ng/ml Amy797E, was also included in the analysis as the baseline, above which the results would be considered positive. Results are shown in the following table. The optical density (OD) at 450 nm was used to evaluate the positive signal to noise ratio. Anything above the reference OD of 0.065 was considered positive.

| Sample # | Replicate | Mean OD | Positive/ Negative Controls |
|---|---|---|---|
| reference |   | 0.065 |   |
| 1 | 1 | 0.038 | Negative |
|   | 2 | 0.036 | Negative |
| 2 | 1 | 0.434 | Positive |
|   | 2 | 0.821 | Positive |
| 3 | 1 | 0.034 | Negative |
|   | 2 | 0.036 | Negative |
| 4 | 1 | 0.673 | Positive |
|   | 2 | 2.664 | Positive |
| 5 | 1 | 0.223 | Positive |
|   | 2 | 0.080 | Positive |
| 6 | 1 | 0.037 | Negative |
|   | 2 | 0.035 | Negative |
| 7 | 1 | 0.041 | Negative |
|   | 2 | 0.033 | Negative |
| 8 | 1 | 0.23 | Positive |
|   | 2 | 0.145 | Positive |
| 9 | 1 | 0.035 | Negative |
|   | 2 | 0.036 | Negative |
| 10 | 1 | 0.037 | Negative |
|   | 2 | 0.039 | Negative |
| 11 | 1 | 0.120 | Positive |
|   | 2 | 0.131 | Positive |
| 12 | 1 | 0.123 | Positive |
|   | 2 | 0.435 | Positive |

The limit of detection (LOD) was calculated using the mean OD values from the negative controls plus three standard deviations. An OD of 0.043 or lower captures 99% of negative samples, indicating that the probability of a false negative is low. These results demonstrate the sensitivity of the methodology, which can reliably detect the presence of the Amy797E protein at a level of 1:1000 maize kernels.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the list of the foregoing embodiments and the appended claims.

What is claimed is:

1. An improved method of extraction and detection of the enzyme Amy797E from a biological sample, wherein the biological sample comprises maize transgenic event 3272, comprising:
   a) homogenizing the biological sample in the presence of extraction buffer and a solubility-promoting compound, wherein the solubility-promoting compound is an amylolytic enzyme;
   b) incubating the sample to permit solubilization of the enzyme Amy797E; and
   c) centrifuging the sample to separate the soluble and insoluble fractions, wherein the enzyme Amy797E fractionates into the soluble fraction, and
   d) detecting the enzyme Amy797E in the soluble fraction by immunoassay, wherein the enzyme Amy797E extracted from the biological sample can be detected with a limit of detection of no greater than 1:1000 maize kernels.

* * * * *